(12) United States Patent
Wrenn, Jr.

(10) Patent No.: US 6,800,616 B2
(45) Date of Patent: Oct. 5, 2004

(54) TREATMENT OF HIV INFECTIONS

(75) Inventor: Simeon M. Wrenn, Jr., Danville, CA (US)

(73) Assignee: SuperGen, Inc., Dublin, CA (US)

(*) Notice: Subject to any disclaimer, the term of this patent is extended or adjusted under 35 U.S.C. 154(b) by 87 days.

(21) Appl. No.: 09/032,881

(22) Filed: Feb. 26, 1998

(65) Prior Publication Data

US 2001/0049359 A1 Dec. 6, 2001

(51) Int. Cl.$^7$ .............................................. A61K 31/70
(52) U.S. Cl. ............................ 514/43; 514/45; 514/46; 514/47; 514/48; 514/49; 514/50; 514/51
(58) Field of Search ............................. 514/43, 45, 46, 514/47, 48, 49, 50, 51

(56) References Cited

U.S. PATENT DOCUMENTS

| | | | |
|---|---|---|---|
| 4,565,696 A | 1/1986 | Heath et al. ................... 424/88 |
| 4,713,372 A | 12/1987 | Schaumberg et al. .......... 514/45 |
| 4,912,092 A | 3/1990 | Gruber ......................... 514/45 |
| 4,997,818 A | 3/1991 | McCaffrey et al. ............. 514/45 |
| 5,017,566 A | 5/1991 | Bodor .......................... 514/58 |
| 5,026,687 A | * 6/1991 | Yarchoan et al. .............. 514/45 |
| 5,087,618 A | 2/1992 | Bodor .......................... 514/45 |
| 5,177,064 A | 1/1993 | Bodor .......................... 514/51 |
| 5,250,529 A | 10/1993 | Theoharides ................. 514/255 |
| 5,292,725 A | 3/1994 | Prendergast .................. 514/46 |
| 5,306,809 A | 4/1994 | Boon et al. ................... 530/363 |
| 5,366,960 A | 11/1994 | Gallagher ..................... 514/43 |
| 5,459,256 A | 10/1995 | Marquez et al. .......... 536/27.14 |
| 5,484,809 A | 1/1996 | Hostetler et al. ............. 514/409 |
| 5,521,162 A | 5/1996 | Jarvi et al. .................... 514/46 |
| 5,541,232 A | 7/1996 | Howell et al. ............... 514/731 |
| 5,618,803 A | 4/1997 | Bodor .......................... 514/81 |
| 5,654,287 A | 8/1997 | Prakash et al. ................ 514/49 |
| 5,663,155 A | 9/1997 | McCaffrey et al. ............ 514/45 |
| 5,679,648 A | 10/1997 | McCaffrey et al. ............ 514/46 |
| 5,681,831 A | 10/1997 | Prendergast .................. 514/46 |
| 5,693,771 A | 12/1997 | Alexander et al. .......... 536/18.6 |
| 5,700,785 A | 12/1997 | Suhadolnik et al. ........... 514/44 |
| 5,843,912 A | * 12/1998 | Hosmane et al. .............. 514/43 |
| 6,277,830 B1 | * 8/2001 | Ganguly et al. |

FOREIGN PATENT DOCUMENTS

JP 88215769 3/1990

OTHER PUBLICATIONS

Sachs, Ach Intern Med., vol. 152, Mar. 1992.*

Ahluwalia et al., Molec. Pharm, vol. 46, pp. 1002–1008 (1994).*

H. Showalter et al., "Adenosine Deaminase Inhibitors. Synthesis and Biological Evaluation of (±)–3,6,7,8–Tetrahydro–3–[(2–hydroxyethoxy)methyl]imidazo[4,5–d][1,3]diazepin–8–ol and Some Selected C–5 Homologues of Pentostatin", J. Med. Chem., 26:1478–1482 (1983).

I. Antonini et al., "Adenosine Deaminase Inhibitors. Synthesis of Deaza Analogues of erythro–9–(2–Hydroxy–3–nonyl)adenine", J. Med. Chem., 27:274–278 (1984).

G. Wolberg et al., "Effects of Adenosine Deaminase Inhibitors on Lymphocyte–mediated Cytolysis", Ann. N.Y. Acad. Sci, 451:215–226 (1985).

D. Saito et al., "Effect of Adenosine deaminase inhibitors on myocardial reactive hyperaemia following brief coronary occlusions", Cardiovas. Res., 19:578–583 (1985).

R. Jackson et al. "The biochemical pharmacology of (2'–R)–chloropentostatin, a novel inhibitor of adenosine deaminase", Adv. Enzyme Regul. 25:125–139 (1986). (Abstract).

C. Dearden et al. "Membrane phenotype and response to deoxycoformycin in mature T cell malignancies", Brit Med. J., 295:873–875 (Oct. 1987).

T. Haertle et al., "Metabolism and Anti–human Immunodeficiency Virus–1 Activity of 2–Halo–2',3'–dideoxyadenosine Derivatives", J. Bio. Chem., 263(2):5870–5878 (Apr. 25, 1988).

G. Cristalli et al., "Adenosine Deaminase Inhibitors. Synthesis and Biological Activity of Deaza Analogues of erythro–9–(2–Hydroxy–3–nonyl)adenine", J. Med. Chem., 31:390–393 (1988).

E. Copelan et al., "Pharmacologic Marrow Purging in Murine T Cell Leukemia", Blood, 71(6):1656–1661 (Jun. 1988).

(List continued on next page.)

Primary Examiner—James O. Wilson

(57) ABSTRACT

Disclosed is a method of treating an HIV-infected host including administering to the host a therapeutic agent that is cytotoxic or cytostatic with respect to CD4+ T cells, but has reduced cytotoxic or cytostatic activity with respect to T lymphocyte stem cells, in a CD4+ T cell cytotoxic or cytostatic effective amount. Also disclosed is a method of treating an HIV-infected host including administering highly active antiretroviral therapy; and coadministering to the host a therapeutic agent that is cytotoxic or cytostatic with respect to CD4+ T cells, but has reduced cytotoxic or cytostatic activity with respect to T lymphocyte stem cells, in a CD4+ T cell cytotoxic or cytostatic effective amount. Also disclosed is a method of ex vivo or in vitro treatment of blood derived cells, bone marrow transplants, or other organ transplants including treating the blood derived cells, bone marrow transplants, or other organ transplants with a therapeutic agent that is cytotoxic or cytostatic with respect to CD4+ T cells, but has reduced cytotoxic or cytostatic activity with respect to T lymphocyte stem cells, in a CD4+ T cell cytotoxic or cytostatic effective amount. Kits and compositions useful in the practice of the invention are also disclosed.

11 Claims, No Drawings

OTHER PUBLICATIONS

I. Fabian et al., "The Effect of Deoxycoformycin on Bone Marrow Cells Treated with Adenosine and Deoxyadenosine and Hemopoietic Growth Factors", *Human Immun.*, 21:81–87 (1988).

W. Sheridan et al., "Preclinical studies on deoxycoformycin and deoxyadenosine as pharmacologic T cell purging tools" *Bone Marrow Trans.*, 4:511–517 (1989).

R. Steis et al., "Kinetics of Recovery of CD4+T cells in Peripheral Blood of Deoxycoformycin–Treated Patients", 83(22):1678–1679 (Nov. 1991).

G. Cristalli et al., "Adenosine Deaminase Inhibitors: Synthesis and Structure—Activity Relationships of Imidazole Analogues of erythro–9–(2–Hydroxy–3–nonyl)adenine", *J. Med. Chem.*, 34:1187–1192 (1991).

C. Dearden et al., "Deoxycoformycin in the treatment of mature T–cell leukaemias", *Brit. J. Can.*, 64(5):903–906 (Nov. 1991).

J. Johnston et al., "Induction of Apoptosis in CD4+ Prolymphocytic Leukemia By Deoxyadenosine And 2'–Deoxycoformycin", 16(8):781–788 (1992).

K. Tobinai et al., "Phase 1 Study of YK–176 (2'–Deoxycoformycin) in Patients with Adult T–cell Leukemia–lymphoma", *Jpn J. Clin. Oncol.*, 22(3):164–171 (1992).

G. Sandhu et al., "Adenosine deaminase inhibitors attenuate ischemic injury and preserve energy balance in isolated guinea pig heart", *Am. J. Physiol.*, 265(4):H1249–1256 (Oct. 1993).

G. Cristalli et al., "Adenosine Deaminase Inhibitors: Synthesis and Structure–Activity Relationships of 2–Hydroxy–3–nonyl Derivatives of Azoles", *J. Med. Chem.*, 37:201–205 (1994).

G. Harriman et al., Adenosine Deaminase Inhibitors. Synthesis and Biological Evaluation of 4–Amino–1–(2(S)–hydroxy–3(R)–nonyl)–1H–imidazo[4,5–c]pyridine (3Deaza–(+)–EHNA) and Certain C1' Derivatives, *J. Med. Chem.*, 37:305–308 (1994).

C. Vargeese et al., "Adenosine Deaminase Inhibitors. Synthesis and Biological Evaluation of Putative Metabolites of (+)–erythro–9–(2S–Hydroxy–3R–nonyl)adenine", *J. Med. Chem.*, 37:3844–3849 (1994).

G. Ahluwalia et al., "Enhancement by 2'–Deoxycoformycin of the 5'–Phosphorylation and Anti–Human Immunodeficiency Virus Activity of 2',3'–Dideoxyadenosine and 2'–β–Fluoro–2',3'–dideoxyadenosine", *Molecul.Pharm.*, 46:1002–1008 (1994).

G. Dighiero, "Potential Immunological Action of Purine Nucleoside Analogues", *Drugs*, 47(6):57–62 (1994).

M. Thali, "Cyclosporins: immunosuppressive drugs with anti–HIV–1 activity", *Mol. Med. Today*, 1(6):287–291 (Sep. 1995). (Abstract).

R Goldschmidt et al., "Antiretroviral drug treatment for HIV/AIDS", 54(2):574–580 (Aug. 1996).

G. Dighiero, "Adverse and beneficial immunological effects of purine nucleoside analogues", *Hematol. Cell. Ther.*, 38:S75–S81, (1996).

T. Chun et al., "Presence of an inducible HIV–1 latent reservoir during highly active antiretroviral therapy", *Proc. Natl. Acad. Sci.*, 94:13193–13197 (Nov. 1997).

J. Seymour et al., "Response duration and recovery of CD4+ lymphocytes following deoxycoformycin in interferon–α–resistant hairy cell leukemia: 7–year follow–up", *Leukemia*, 11:42–47 (1997).

C. Gorman, "The Odds Grow Longer", *Time* (Nov. 24, 1997).

N. Llewellyn–Smith et al., "Effects of anti–CD4 antibody treatment on lymphocyte subsets and stimulated tumor necrosis factor alpha production:a study of 29 multiple sclerosis patients entered into a clinical trial of cM–T412", *Neurology*, 48(4):810–816 (Apr. 1997). (Abstract).

J. Wong et al., "Recovery of Replication–Competent HIV Despite Prolonged Suppression of Plasma Viremia", *Science*, 278:1291–1295 (Nov. 14, 1997).

V. DeVita, Jr., et al., *Cancer Principles & Practice of Oncology*, pp. 57–59, 63–65, 2621–2634 (1993).

R. Gulick, "Current antiretroviral therapy: an overview", *Qual Life Res*, 6(6):471–474 (Aug. 1997).

K. Henry et al., "Antiretroviral therapy for HIV infection. Heartening successes mixed with continuing challenges", *Postgrad Med*, 102(4):100–107, (Oct. 1997).

C. Hicks, "Update on antiretroviral therapy", *Radiol. Clin. North. Am.*, 35(5):995–1005, (Sep. 1997).

D. Greiner et al., "Pentostatin (2'–deoxycoformycin) in the treatment of cutaneous T–cell lymphoma", *J. Am. Acad. Derm.*, 36(6):950–955 (Jun. 1997).

M. Oldstone, "HIV versus Cytotoxic T Lymphocytes—The War Being Lost", *N. Eng. J. Med.*, 337(18):1306–1308 (Oct. 1997).

K. Morris, "New Angles sought as HIV–1 evades combined therapy", *The Lancet*, 350(9090):1523–1524 (Nov. 22, 1997).

D. Finzi et al., "Identification of a Reservoir for HIV–1 in Patients on Highly Active Antiretroviral Therapy", *Science*, 278:1295:1300 (Nov. 14, 1997).

M. Balter, "HIV Survives Drug Onslaught by Hiding Out in T Cells", *Science*, 278:1227 (Nov. 14, 1997).

M. Balter, "How Does HIV Overcome the Body's T Cell Bodyguards?", *Science*, 278:1399–1400 (Nov. 21, 1997).

F. Dumont et al., "A Tacrolimus–related Immunosuppressant with Reduced Toxicity", *Transplantation*, 65(1):18–26 (Jan. 15, 1998).

Hayashi et al., "In–Vitro ingibition of the infectivity and replication of HIV by 2'–3'–deoxynucleosides and viral binding inhibitors"; vol. 37, No. 2, 1989; pp. 411 (abstract).

Sachs, M.K., "Antiretroviral Chemotherapy of HiV Infections Other Than With AZT", vol. 152, No. 3; 1992;pp. 485–501.

Ruxrungtham et al., "Potent Activity of 2'–beta–fluoro–2'–3'–dideoxyadenosine Against HIV–1 Infection in HU–PBL–SCID mice"; vol. 40, No. 10; 1996, pp. 2369–2374.

US F.D.A.: SCRIP; vol. 1360, Nov. 1988; pp 30.

Nakashima et al., "Anti–HIV–1 Activity of Antiviral Compounds, As Quantitated by a Focl Immunoassay in CD4+ Hela Cells and a Plaque Assay in MT–4 Cells"; vol. 29, No. 2; 1990, pp. 978–985.

Database Aidsline; Online!; Feb. 1998, Welles et al., "A Phase I Study of 2'–beta–flour–2',3'–dideoxyadenosine in Patients With Symptomatic HIV Infection"; Meeting Abstract Clinical Trials Phase I, 1998, pp. 202.

* cited by examiner

TREATMENT OF HIV INFECTIONS

BACKGROUND OF THE INVENTION

1. Field of the Invention

This invention relates to methods of treating HIV and AIDS.

2. Description of Related Art

Current therapies for Human Immunodeficiency Virus (HIV) infections are typically built around highly active antiretroviral therapy (HAART). HAART therapies are often combinations or "cocktails" of two or more antiretroviral agents. R. M. Gulick, "Current antiretroviral therapy: an overview", Qual. Life Res. 6(6):471–474 (1997); K. Henry et al., "Antiretroviral therapy for HIV infection. Heartening Successes mixed with continuing challenges", Postgrad. Med. 102(4):100–107 (1997); C. B. Hicks, "Update on antiretroviral therapy", Radiol. Clin. North Am. 35(5):995–1005 (1997); R. H. Goldschmidt, "Antiretroviral drug treatment for HIV/AIDS", Am. Fam. Physician, 54(2):574–580 (1996). Drugs used in HAART regimens include the nuceloside analogs AZT, stavudine (d4T), and 3TC; nevirapine (a non-nucleoside reverse transcriptase inhibitor, which may be abbreviated NVP), and protease inhibitors such as RTV, SQV, IDV, and nelfinavir. HAART using these treatments may reduce plasma loads of active HIV virus in HIV-1-positive patients to undetectable amounts, apparently without the threat of developing resistant strains of HIV. M. Balter, "HIV Survives Drug Onslaught by Hiding Out in T Cells," Science 278:1227 (Nov. 14, 1997). This document, and all documents cited to herein, are incorporated by reference as if fully reproduced below.

The hope was that if active HIV replication was suppressed through HAART for a sufficiently long period, say three years or so, the virus would be completely removed. However, it appears that reducing the plasma concentration of active HIV is not sufficient to eradicate HIV infection completely.

In three studies, memory CD4+ cells were isolated from patients undergoing HAART, most of whom had undetectable plasma HIV-1. Memory CD4+ T cells are CD4+CD8- T lymphocytes that are "resting" or quiescent. These memory cells are generally non-proliferating, and are capable of being activated in case of a subsequent exposure to an antigen. In this way, they form part of the acquired immune response. Further information describing memory T cells can be found in a standard immunology textbook, such as E. Benjamin, et al., "Immunology: A Short Course," (1996) (Wiley-Liss). Previous investigators had detected integrated viral DNA in memory T cells, but believed it to be defective. The investigators in the three studies found that once the memory T cells were activated, replication-competent HIV-1 was produced in most cases.

In the first study, replication competent virus was routinely recovered from memory CD4+ T lymphocytes of 22 patients who had been treated successfully with HAART for up to 30 months. The frequency of latently infected cells was low, but these frequencies did not decrease with increasing time on therapy, indicating long-term survival of latently infected cells. D. Finzi, et al., "Identification of a Reservoir for HIV-1 in Patients on Highly Active Antiretroviral Therapy", Science 278:1295 (Nov. 14, 1997).

In the second study, investigators found that highly purified memory CD4+ T cells from patients receiving HAART for an average of ten months were capable of producing infectious virus upon cellular activation in vitro. They also found unintegrated HIV-1 DNA in the memory T cells, which they suggest shows persistent active virus replication in vivo. T-W Chun et al., "Presence of an Inducible HIV-1 Latent Reservoir During Highly Active Antiretroviral Therapy", Proc. Natl. Acad. Sci. 94:13193–97 (1997).

In the third study, researchers took blood cells from HIV-positive patients undergoing HAART for up to two years and cultured them together with blood cells from HIV-negative donors, along with reagents that trigger memory T cells to become immunologically activated. The researchers observed virus from latently infected memory cells quickly infecting and replicating in the HIV-negative cells, even though the original level of infection of the HIV-positive cells was very low. J. Wong et al., "Recovery of Replication-Competent HIV Despite Prolonged Suppression of Plasma Viremia", Science 278:1291 (1997).

These results imply that the reservoirs of integrated and unintegrated HIV existing in memory T cells can potentially reestablish active HIV infection and AIDS. These results agree with earlier findings that removing patients from HAART may reestablish active HIV infection and AIDS.

However, conventional HAART does not reach these memory T cells. The drugs that make up HAART's are focused on actively replicating HIV in proliferating T cells and other proliferating immune system cells, such as macrophages. The drugs function by inhibiting virus replication and infection, and by inhibiting or killing infected proliferating cells. Accordingly, it does not seem likely that continued administration of HAART will reach the memory T cell HIV reservoir to eradicate the integrated and unintegrated virus contained within it.

There is therefore a need for methods, kits, and compositions that can address the existence of the HIV reservoir in memory T cells.

SUMMARY OF THE INVENTION

In one aspect, the invention relates to a method of treating an HIV-infected host comprising administering to the host a therapeutic agent that is cytotoxic or cytostatic with respect to CD4+ T cells, but has reduced cytotoxic or cytostatic activity with respect to T lymphocyte stem cells, in a CD4+ T cell cytotoxic or cytostatic effective amount.

In another aspect, the invention relates to a method of treating an HIV-infected host comprising administering highly active antiretroviral therapy; and coadministering to the host a therapeutic agent that is cytotoxic or cytostatic with respect to CD4+ T cells, but has reduced cytotoxic or cytostatic activity with respect to T lymphocyte stem cells, in a CD4+ T cell cytotoxic or cytostatic effective amount.

In yet another aspect, the invention relates to a kit comprising a therapeutic agent that is cytotoxic or cytostatic with respect to CD4+ T cells, but has reduced cytotoxic or cytostatic activity with respect to T lymphocyte stem cells, wherein the therapeutic agent is present in a CD4+ T cell cytotoxic or cytostatic effective amount.

In a further aspect, the invention relates to a composition comprising a therapeutic agent that is cytotoxic or cytostatic with respect to CD4+ T cells, but has reduced cytotoxic or cytostatic activity with respect to T lymphocyte stem cells, wherein the therapeutic agent is present in a CD4+ T cell cytotoxic or cytostatic effective amount.

In still another aspect, the invention relates to a method of ex vivo or in vitro treatment of blood derived cells, bone marrow transplants, or other organ transplants comprising treating the blood derived cells, bone marrow transplants, or other organ transplants with a therapeutic agent that is cytotoxic or cytostatic with respect to CD4+ T cells, but has reduced cytotoxic or cytostatic activity with respect to T lymphocyte stem cells, in a CD4+ T cell cytotoxic or cytostatic effective amount.

DETAILED DESCRIPTION OF THE INVENTION

In one aspect, the invention relates to a method of treating an HIV-infected host comprising: administering to the host a therapeutic agent that is cytotoxic or cytostatic with respect to CD4+ T cells, but has reduced cytotoxic or cytostatic activity with respect to T lymphocyte stem cells, in a CD4+ T cell cytotoxic or cytostatic effective amount.

In another aspect, the invention relates to the above method, where the therapeutic agent comprises a nucleoside analog, or a CD4+ T cell specific antibody alone or coupled or conjugated to a moiety that is cytotoxic or cytostatic with respect to CD4+ T cells.

In one aspect, the invention relates to the above method, wherein the nucleoside analog comprises purine and pyrimidine and their analogs thereof. In a further aspect, the invention relates to the method, where the nucleoside analog comprises pentostatin and analogs thereof, coformycin, cladribine, fludarabine, or a deoxyadenosine and analogs thereof. In another aspect, the invention relates to the method, where the therapeutic agent comprises pentostatin and analogs thereof.

In a further aspect, the invention relates to the method where the CD4+ T cell comprises a memory cell. In another aspect, the invention relates to the method, where the CD4+ T cells comprise both HIV-infected and non-HIV-infected CD4+ T cells. In a further aspect, the invention relates to the method where the antibody is specific for CD4+ memory T cells. In yet another aspect, the invention relates to the method further comprising reestablishing the host's immune system. In still another aspect, the invention relates to the method, wherein the step of reestablishing the host's immune system comprises providing bone marrow transplants, thymic stimulation, administration of various cytokine growth factors, vaccination, or administration of interleukins.

Another aspect of the invention is a method of treating an HIV-infected host comprising administering highly active antiretroviral therapy; and coadministering to the host a therapeutic agent that is cytotoxic or cytostatic with respect to CD4+ T cells, but has reduced cytotoxic or cytostatic activity with respect to T lymphocyte stem cells, in a CD4+ T cell cytotoxic or cytostatic effective amount.

In a further aspect, the invention relates to the method, where the therapeutic agent comprises a nucleoside analog, or a CD4+ T cell specific antibody alone or coupled or conjugated to a moiety that is cytotoxic or cytostatic with respect to CD4+ T cells. In still another aspect, the invention relates to the method, wherein the nucleoside analog comprises purine and pyrimidine and their analogs thereof. In a further aspect, the invention relates to the method, where the nucleoside analog comprises pentostatin and analogs thereof, coformycin, cladribine, fludarabine, or a deoxyadenosine and analogs thereof. In an alternate aspect, the invention relates to the method, where the therapeutic agent comprises pentostatin and analogs thereof.

In a further aspect, the invention relates to the method where the CD4+ T cell comprises a memory cell. In yet another aspect, the invention relates to the method, where the CD4+ T cells comprise both HIV-infected and non-HIV-infected CD4+ T cells. In an aspect, the invention relates to the method where the antibody is specific for CD4+ memory T cells.

In a further aspect, the invention relates to the method, wherein the therapeutic agent according to the invention is administered or coadministered parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In yet another aspect, the invention relates to the method, wherein the therapeutic agent is administered or coadministered singly or as a combination with another therapeutic agent. In a further aspect, the invention relates to the method, wherein the combination comprises a deoxyadenosine and pentostatin. In yet a further aspect, the invention relates to the method, wherein the combination comprises 2',3'-dideoxyadenosine and pentostatin.

In a further aspect, the invention relates to the method, wherein the therapeutic agent is pentostatin, and the pentostatin is administered or coadministered intravenously in doses of about four to ten mg/sq m once per day for about three consecutive days once per month, about four to five mg/sq m/day weekly for about four weeks and about fortnightly thereafter, to the generally frequented dose of about four mg/sq m about every two weeks for a maximum dosage period of about one year.

In an aspect, the invention relates to a kit comprising a therapeutic agent that is cytotoxic or cytostatic with respect to CD4+ T cells, but has reduced cytotoxic or cytostatic activity with respect to T lymphocyte stem cells, wherein the therapeutic agent is present in a CD4+ T cell cytotoxic or cytostatic effective amount. In another aspect, the invention relates to the kit, where the therapeutic agent comprises a nucleoside analog, or a CD4+ T cell specific antibody alone or coupled or conjugated to a moiety that is cytotoxic or cytostatic with respect to CD4+ T cells. In still another aspect, the invention relates to the kit, wherein the nucleoside analog comprises purine and pyrimidine and their analogs thereof. In a further aspect, the invention relates to the kit, where the nucleoside analog comprises pentostatin and analogs thereof, coformycin, cladribine, fludarabine, or a deoxyadenosine and analogs thereof. In still another aspect, the invention relates to the kit, where the therapeutic agent comprises pentostatin and analogs thereof.

In one aspect, the invention relates to a composition comprising a therapeutic agent that is cytotoxic or cytostatic with respect to CD4+ T cells, but has reduced cytotoxic or cytostatic activity with respect to T lymphocyte stem cells, wherein the therapeutic agent is present in a CD4+ T cell cytotoxic or cytostatic effective amount.

In another aspect, the invention relates to the composition, where the therapeutic agent comprises a nucleoside analog, or a CD4+ T cell specific antibody alone or coupled or conjugated to a moiety that is cytotoxic or cytostatic with respect to CD4+ T cells. In still another aspect, the invention relates to the composition, wherein the nucleoside analog comprises purine and pyrimidine and their analogs thereof. In yet another aspect, the invention relates to the composition, where the nucleoside analog comprises pentostatin and analogs thereof, coformycin, cladribine, fludarabine, or a deoxyadenosine and analogs thereof. In a further aspect, the invention relates to the composition, where the therapeutic agent comprises pentostatin and analogs thereof.

In an aspect, the invention relates to a method of ex vivo or in vitro treatment of blood derived cells, bone marrow transplants, or other organ transplants comprising treating the blood derived cells, bone marrow transplants, or other organ transplants with a therapeutic agent that is cytotoxic or cytostatic with respect to CD4+ T cells, but has reduced cytotoxic or cytostatic activity with respect to T lymphocyte stem cells, in a CD4+ T cell cytotoxic or cytostatic effective amount.

In another aspect, the invention relates to the method, where the therapeutic agent comprises a nucleoside analog, or a CD4+ T cell specific antibody alone or coupled or conjugated to a moiety that is cytotoxic or cytostatic with respect to CD4+ T cells. In still another aspect, the invention relates to the method, wherein the nucleoside analog comprises purine and pyrimidine and their analogs thereof. In yet another aspect, the invention relates to the method, where the nucleoside analog comprises pentostatin and analogs thereof, coformycin, cladribine, fludarabine, or a deoxyadenosine and analogs thereof. In a further aspect, the invention relates to the method, where the therapeutic agent comprises pentostatin and analogs thereof.

In the course of further discussing the invention, the inventor does not wish to be bound by a particular mechanism or explanation of action, as such understanding is not necessary for the practice of the invention. Within this context, however, the inventor hypothesizes that administering to the host (or patient) a therapeutic agent that is cytotoxic or cytostatic with respect to CD4+ T cells, but is not cytotoxic or cytostatic, or has reduced such activity, with respect to T lymphocyte stem cells, in a cytotoxic or cytostatic effective amount, may eliminate or reduce the reservoir of HIV-infected memory T cells. This is particularly true if the host is in need of this treatment or (co) administration, etc.

At this point, an overview of how the invention might be practiced in one preferred embodiment may be helpful. In one preferred embodiment, an HIV positive patient receives HAART, together with appropriate pharmaceuticals, such as antivirals; antifungals; and antibiotics, to protect against opportunistic infections. Additionally, the patient is coadministered one or more therapeutic agents, according to the invention. This regimen is continued for a period past the point when the levels of integrated and unintegrated HIV in active and memory T cells are undetectably low. At the end of the period, the patient is weaned from HAART and from the therapeutic agents according to the invention. At this point, the patient is monitored for reestablishment of normal immune function and for signs of reemergence of HIV infection. Additionally, any needed conjunctive immunotherapy, such as bone marrow transplants, various cytokines or vaccination, is administered. If there are no signs of HIV infection for a suitable period, then the patient is weaned from the pharmaceuticals that protect against opportunistic infections. After this, the patient is monitored on a routine basis for life to detect reemergence of HIV infection, in which case repeat therapy according to the above preferred embodiment must be undertaken The various aspects of practicing the invention will now be discussed in more detail. Patients suffering from HIV infections are often treated using a combination of HAART and various other pharmaceuticals. These other pharmaceuticals may be coadministered with the HAART for a variety of reasons, including treating the opportunistic infections that can be common in HIV patients. Coadministration in the context of this invention is defined to mean the administration of more than one therapeutic in the course of a coordinated treatment to achieve an improved clinical outcome. Such coadministration may also be coextensive, that is, occurring during overlapping periods of time. Further discussion of such conventional treatment can be found in R. M. Gulick, "Current antiretroviral therapy: an overview", Qual. Life Res. 6(6):471–474 (1997); K. Henry et al., "Antiretroviral therapy for HIV infection. Heartening Successes mixed with continuing challenges", Postgrad. Med. 102(4):100–107 (1997); C. B. Hicks, "Update on antiretroviral therapy", Radiol. Clin. North Am. 35(5):995–1005 (1997); R. H. Goldschmidt, "Antiretroviral drug treatment for HIV/AIDS", Am. Fam. Physician, 54(2):574–580 (1996).

The present invention may serve as an adjunct to this conventional therapy through coadministration. In an alternative embodiment, the present invention may be practiced apart from conventional therapy, if appropriate. The nature of the inventive therapeutic agents is such that their administration or coadministration may have an antiviral effect. Such an antiviral effect may be additive, in the case of coadministration with HAART, or it may be the primary antiviral effect afforded the patient. In either situation, performing treatment on HIV-infected patients according to the invention is an important advance because the inventive treatment reaches memory cells.

Memory cells are a particularly difficult target to reach with most conventional anti-HIV therapies. As noted above, such therapies are most effective against HIV in proliferating cells. Such cells are much more interactive with their environment, and thus offer more opportunity for exogenous intervention. In fact, prior to this invention, approaches to HIV therapy were focused on such proliferating cells almost exclusively, because of the relative ease of intervention.

However, to reach memory cells, which are by definition non-proliferating until activated, non-conventional approaches are needed. Accordingly, the invention provides for therapeutic agents that have cytotoxic or cytostatic effects with respect to memory cells. These inventive therapeutic agents are characterized by their differential ability to affect non-proliferating T lymphocytes, as compared to conventional HIV therapies.

For example, the inventive therapeutic agents may intervene in essential cellular structure that is not involved in cell replication. In one instance, therapeutic agents according to the invention may accelerate non-replicating DNA strand breaks, consequently inducing apoptosis. Additionally, inventive therapeutic agents might induce lysis of resting/memory cells by selectively binding to and disrupting the membrane of memory cells.

It should be noted that the cytotoxic or cytostatic effects of the therapeutic agents according to the invention include both apoptosis and classic cell death (eg. lysis, etc.) mechanisms.

Alternatively, the therapeutic agents may selectively activate apoptotic genes in memory cells, resulting in programmed cell death. This may be accomplished, for example, by providing therapeutic agents that are taken up selectively by memory cells and intervene in the regulatory pathways of the memory T cell's apoptotic genes.

In another approach, inventive therapeutic agents may selectively modify a memory cell's ability to adapt to environmental stresses, such as endogenous toxins (e.g. free radicals). This renders the memory cells particularly vulnerable to the introduction of such environmental stresses, and leads to the differential cell death of such cells.

Another class of inventive therapeutic agents may act by selectively activating the host's reservoir of memory cells.

Such activated T cells may begin proliferating, thus exposing any integrated or unintegrated HIV to conventional HAART. This allows use of HAART to eliminate or reduce the reservoir of HIV contained in the memory cell pool.

Classes of therapeutic agents that fall into one or more of the above categories are available to one of skill in the art. It is a particular sign of the non-obviousness of this invention that the effect of such therapeutic agents on CD4+ subset (including memory) cells was previously seen as a deleterious side effect, rather than a desirable property. This is because, for example, the apparent objective of previous anti-HIV therapies was to eradicate the virus without doing further damage to the patient's immune system. In the case of the present invention, a portion of the patient's immune system is actually further damaged in order to reduce or eliminate a previously unreachable reservoir of HIV.

Take, for example, nucleoside analogs. Such analogs have been used in a variety of applications, including antiviral and oncological applications. In these applications, any potential side effects that differentially targeted memory cells, such as loss of acquired immunity, were seen as undesirable. However, in the context of this invention, loss of acquired immunity through the elimination of memory T cells, is a potentially desirable condition.

Nucleoside analogs useful in this invention include analogs containing purine and pyrimidine, and their analogs thereof. Included within the definition of analogs are various prodrugs of the active species. Development of such prodrugs may be according to methods known in the art. Additional information may be found in U.S. Pat. No. 5,177,064 to Bodor, and in U.S. Pat. No. 5,459,256 to Marquez et al.

Preferred nucleoside analogs include analogs containing adenine, guanine, cytosine, uracil, and thymine, and their analogs thereof. Among these, 2'-deoxycoformycin (also referred to as DCF, pentostatin, or NIPENT®), an inhibitor of adenosine deaminase; fludarabine monophosphate (FLU), a fluorinated analogue of adenine that is relatively resistant to adenosine-deaminase and 2-chloro-2'-deoxyadenosine (also known as cladribine or 2CDA) a drug also resistant to adenosine deaminase through introduction of a chloride at the carbon 2, are especially preferred. Also especially preferred are deoxyadenosines generally, including 2'-deoxyadenosine, 3'-deoxyadenosine, and dideoxyadenosine.

The analogs according to the invention have demonstrated activity against quiescent, resting, lymphocytes (i.e. memory cells). For example, upon administering DCF, FLU or 2CDA, prolonged lymphopenia predominating in T cells, especially in the CD4+ subset, and an increased frequency of opportunistic infections has been observed. Byrd, J. C. et al., "Fatal recurrence of autoimmune hemolytic anemia following pentostatin therapy in a patient with a history of fludarabine-associated hemolytic anemia." *Ann Oncol,* 6:300–301 (1995); Cheson, B. D., "Infectious and immunosuppressive complications of purine analog therapy." *J. Clin. Oncol.* 13:2431–2448 (1995); Kester K., et al., "Fludarabine therapy for lymphoid malignancies is associated with a high number of opportunistic pulmonary infections", *Blood.* 82:138a (1993); Seymour, J. F., et al., "Prolonged CD4+ lymphocytopenia, is the cost of durable responses TO2-chloro-deoxyadenosine (2-CdA) in patients (PTS) with hairy cell leukemia (HCL)(abstract), *Blood,* 82:142a (1993). Additionally, work from Carson et al. demonstrated that 2CDA could selectively harm resting normal human lymphocytes. Carson, D. A., et al., "Specific toxicity of 2-clorodeoxyadenosine toward resting and proliferating human lymphocytes", *Blood,* 62:737–743 (1983).

While not wishing to be bound by a particular mechanism or explanation, it appears that the adenosine analogs, at least, act through the T cell's adenosine deaminase pathways. Dighiero, G., "Adverse and beneficial immunological effects of purine nucleoside analogues," *Hematol Cell Ther,* 38:575–581 (1996). In humans, a genetic deficiency of adenosine deaminase (ADA) may cause severe combined immunodeficiency. ADA is characterized by a selective lymphopenia of both T and B cells resulting in reduced cellular and humoral immune capacity, which may be attributed to the toxic effect of deoxyadenosine accumulation.

Available evidence indicates, however, that T cells might be more sensitive than B cells to intervention in the ADA pathway. ADA levels have been found to be tenfold greater in T cells than in B cells. In addition, it has been shown that ADA inhibition, since T cells display greater dATP accumulation, affects more T than B cells.

While the exact nature of the ADA pathway intervention seems unclear, it may be that analogs of adenosine resistant to cellular deamination might mimic the ADA-deficient state. They would thus have a potential therapeutic activity on resting lymphocytes without damaging other cell types. Lack of ADA seems to lead to a build up of deoxyadenosine and adenosine triphosphate in the cell, thus fatally accelerating DNA strand breaks in the cell.

Under normal conditions, resting lymphocytes are continuously breaking and rejoining DNA. When this physiological process is accelerated by the effect of excess adenosine triphosphate, it leads to consumption of NAD for poly-ADP-ribose synthesis. This polymer is produced from nicotinamide adenosine dinucleotides (NAD) in a reaction catalyzed by the chromatin-associated poly(ADP-ribose) synthetase, leading to a depletion of the NAD content of the cell. This depletion induces a profound alteration of cellular reducing power, because of lethal ADP and ATP depletion.

The result is programmed cell death through activation of a Ca++, Mg++, dependent endonuclease. Hence, it appears that nucleoside analogs according to the invention can act on quiescent lymphocytes via an apoptotic process. The fact that supplementation of a cell medium with the NAD precursor of nicotinamide or 3-aminobenzamide, an inhibitor of poly (ADP-ribose) synthetase, prevented NAD depletion and reduces 2CDA toxicity, tends to support this hypothesis.

The various adenosine analogs affect the ADA pathway in different manners. DCF, for example, has been shown to be an quasi-irreversible inhibitor of ADA. By favoring the predominance of deoxycytidine kinase (DCK) over the dephosphorylating enzyme 5-nucleotidase in lymphocytes it induces a preferential accumulation of deoxyadenosine-5'-triphosphate (dATP). By comparison, FLU and 2CDA are rather resistant to the enzyme. Both drugs are initially phosphorylated by DCK and contribute to the accumulation of cellular adenosine triphosphate. As noted above, the accumulation of adenosine triphosphate, whether by the presumed DCF mechanism, or the FLU or 2CDA mechanism, promotes the apoptotic death of the cell.

Additional discussion of possible mechanisms of various adenosine analogs may be found in C. Dearden, et al., "Deoxycoformycin in the treatment of mature T-cell leukaemias", *Brit J. of Can.,* 64(5):903–906 (November 1991); J. Seymour et al., "Response duration and recovery of CD4+ lymphocytes following deoxycoformycin in interferon-α-resistant hairy cell leukemia: 7-year followup", *Leukemia,* 11, 42–47 (1997); J. Johnston et al., "Induction of Apoptosis in CD4+ Prolymphocytic Leukemia by Deoxyadenosine and 2'-Deoxycoformycin", *Leukemia Research,* 16:8, 781–788 (1992); I. Fabian et al., "The Effect of Deoxycoformycin on Bone Marrow Cells Treated with Adenosine and Deoxyadenosine and Hemopoietic Growth Factors", *Human Immunology,* 21, 81–87 (1988); E. Copelan et al., "Pharmacologic Marrow Purging in Murine T Cell Leukemia", *Blood,* 71(6):1656–1661 (June 1988); W. Sheridan et al., "Preclinical studies on deoxycoformycin and deoxyadenosine as pharmacologic T cell purging tools" *Bone Marrow Trans.* 4:511–517 (1989); S. Sandhu et al., "Adenosine deaminase inhibitors attenuate ischemic injury and preserve energy balance in isolated guinea pig heart", 265(4):1249–1256 (October 1993); D. Saito et al., "Effect of adenosine deaminase inhibitors on myocardial reactive hyperaemia following brief coronary occlusions", *Cardiovascular Research,* 19, 578–583 (1985); G. Cristalli et al., "Adenosine Deaminase Inhibitors: Synthesis and Structure—Activity Relationships of Imidazole Analogues of erythro-9-(2-Hydroxy-3-nonyl)adenine", *J. Med. Chem.* 34:1187–1192 (1991); G. Cristalli et al., "Adenosine Deaminase Inhibitors. Synthesis and Biological Activity of Deaza Analogues of erythro-9-(2-Hydroxy-3-nonyl)adenine", *J. Med. Chem.,* 31: 390–393 (1988); R. Jackson et al., "The Biochemical Pharmacology of (2'-R)-Chloropentostatin, a Novel Inhibitor of Adenosine Deaminase", *Advances in Enzyme Regulation,* 25:125–139; C. Vargeese, et al., "Adenosine Deaminase Inhibitors. Synthesis and Biological Evaluation of Putative Metabolites of (+)-erythro-9-(2S-Hydroxy-3R-nonyl)adenine", *J. Med. Chem.* 37:3844–3849 (1994); G. Wolberg et al., "Effects of Adenosine Deaminase Inhibitors on Lymphocyte-mediated Cytolysis", *Annals of the New York Academy of Sciences,* 451:215–226 (1985); G. Harriman et al., "Adenosine Deaminase Inhibitors. Synthesis and Biological Evaluation of 4-Amino-1-(2(S)-hydroxy-3(R)-nonyl)-1H-imidazo[4,5-c]pyridine(3-Deaza-(+)-EHNA) and Certain C1' Derivatives", *J. Med. Chem.* 37:305–308 (1994); I. Antonini et al., "Adenosine Deaminase Inhibitors. Synthesis of Deaza Analogues of erhythro-9-(2-Hydroxy-3-nonyl)adenine" *J. Med. Chem.* 27:274–278 (1984); G. Cristalli et al., "Adenosine Deaminase Inhibitors: Synthesis and Structure—Activity Relationships of 2-Hydroxy-3-nonyl Derivatives of Azoles", *J. Med. Chem.,* 37:201–205 (1994); and H. Showalter et al., "Adenosine Deaminase Inhibitors. Synthesis and Biological Evaluation of (±)-3,6,7,8-Tetrahydro-3-[2-hydroxyethoxy)methyl] imidazo[4,5,-d][1,3]diazepin-8-ol and Some Selected C-5 Homologues of Pentostatin", *J. Med. Chem.* 26:1478–1482 (1983).

Other therapeutic agents useful in the practice of this invention include cyclosporine, tacrolimulus (FK506), and antibodies directed against specific T-cell epitopes (either alone or conjugated with other agents, such as cytotoxins, radiation/photochemical sensitizers), cytostasis inducing compounds (e.g. radiation/photochemical sensitizers), peptide mimetics that target specific receptors or other proteins on T-cells, analogs of these agents, and other unique pathways that may be amenable to intervention, preferably T-cells, and more preferably CD4+ cells.

A discussion regarding cyclsoporin's anti-HIV activity can be found in M. Thali, "Cyclosporins: immunosuppressive drugs with anti-HIV activity", *Mol. Med. Today,* 1:287–291 (1995). Further discussion of FK 506 and useful FK506 analogs may be found in F. J. Dumont et al., "A tacrolimus-related immunosuppressant with reduced toxicity", *Transplantation* 65(1):18–26 (1998). Examples of useful antibody conjugates may be found, for example, in U.S. Pat. No. 5,306,809 to Boon et al. Additional discussion of useful antibodies and antibody conjugates can be found in S. J. Knox et al., "Treatment of cutaneous T-cell lymphoma with chimera anti-CD4 monoclonal antibodies", *Blood,* 87:839 (1996).

The therapeutic agents according to the invention may be administered or coadministered in any conventional dosage form. For example, they may be administered or coadministered parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, or intrathecally. The therapeutic agents according to the invention may also be administered or coadministered in slow release dosage forms. Furthermore, the therapeutic agents may be administered or coadministered with conventional pharmaceutical excipients and additives.

Additionally, the therapeutic agents may be administered or coadministered singly or in combinations of therapeutic agents. One preferred example of such a combination is the combination of deoxyadenosines with pentostatin. It has been reported that pentostatin enhances the clinical anti-HIV activity of related adenosine analogs presumably due to prevention of degradation of the adenosine analogs by adenosine deaminase. G. S. Ahluwalia, et al., "Enhancement by 2'-deoxycoformycin of the 5'-Phosphorylation and Anti-Human immunodeficiency virus activity of 2'3'-dideoxyadenosine and 2'-beta-fluor-2',3'-dideoxyadenosine", *Molec. Pharmacol.* 46:1002–1008 (1994). Thus in patients already receiving HAART for a period of time to effect reduction in viral load to below detectable levels, therapy may be initiated with pentostatin and 2',3'-dideoxyadenosine combination following cessation of HAART or in combination with HAART. This might be expected to promote further cytotoxic and/or cytostatic activity with respect to CD4+ cells, especially memory cells. This is because combination of deoxyadenosine and pentostatin seem to produce enhanced cytotoxic activity in T-cell malignancies over either drug alone. Thus, such a combination might enhance both antiviral and cytotoxic/cytostatic activity of pentostatin and 2',3'-dideoxyadenosine as compared to either agent alone.

Dosage amounts and frequency will vary according to the particular therapeutic agent, dosage form, and individual patient characteristics. Generally speaking, determining the dosage amount and frequency for a particular therapeutic agent, dosage form, or individual patient characteristic can be accomplished using conventional dosing studies, coupled with appropriate diagnostics.

In one embodiment, pentostatin is used as the therapeutic agent. In this embodiment, pentostatin may be administered or coadministered intravenously in doses of about four to ten mg/sq m once per day for about three consecutive days once per month, about four to five mg/sq m/day weekly for about four weeks and about fortnightly thereafter, to the generally frequented dose of about four mg/sq m about every two weeks for a maximum dosage period of about one year. Of course, this dosing regimen may be adjusted depending upon the individual patient's needs.

After, or during, administering or coadministering the therapeutic agent according to the invention, It may be desirable, in certain circumstances, to continue HAART. Additionally, it may be desirable to continue administering or coadministering drugs for treating the opportunistic infections that can be common in HIV patients. Continuing such treatments helps to keep active virus levels low, especially if the therapeutic agent acts cytotoxically or cytostatically to release virus from the CD4+ active and memory cells. Additionally, continuing such treatments protects the patient, who may be severely immunosuppressed or immunocompromised, against opportunistic infection.

At some point during the course of therapy, it may become appropriate to reduce or even cease HAART and administration or coadministration of the inventive therapeutic agents. Generally, the endpoint might preferably occur when the level of active virus is undetectable and the number of CD4+ T lymphocyte memory cells, especially those containing HIV, is undetectably low. The level of active virus may be considered undetectable low using conventional assays of viral activity, including measuring copies of HIV RNA/ml. The number of CD4+ T lymphocyte memory cells can likewise be determined using conventional assays and screens.

Of course, if drugs forwarding off opportunistic infections are being administered or coadministered, it would not be appropriate to wean a patient from those drugs until the patient's immune system has been appropriately reestablished. Administration or coadministration of HAART and therapeutic agents according to the invention will likely result in loss of some acquired immunity, leaving the patient in an immunosuppressed state.

If the patient's immune system does not spontaneously reemerge from its immunosuppressed state after ceasing HAART and the inventive therapy, then it may be necessary to intervene further. This intervention may take the form of reestablishing the patients immune system through procedures such as bone marrow transplants, thymic stimulation, administration of various cytokine growth factors and/or interleukins, vaccination, and other similar, conventional, procedures. The patient's immune system may be considered reestablished when conventional measures of immune system function have returned to reasonably normal levels.

Reestablishment of the patient's immune system, particularly the CD4+ subset, presupposes the existence of stem cells that are relatively resistant to HIV infection and that can be differentiated so as to resupply the patient with CD4+ T cells. During ontogeny and in T cell development, precursors of T cells migrate from the bone marrow to the thymus, where most T cell development occurs. In the thymus, T cells mature, express antigen specificity and are selected for appropriate antigen binding. More complete discussion of T cell development may be found in "Cancer: Principles and Practice of Oncology" (1997) (Vincent DeVita, et al., eds.)

Practicing the invention as disclosed permits these stem cells to undergo the thymic maturation process and develop into mature CD4+ cells at a significantly reduced risk of HIV infection. Furthermore, it is within the scope of the invention to stimulate the production of stem cells (through, eg., bone marrow transplants), and of mature CD4+ and other immune system components (through various forms of immunostimulation).

After the patient's immune system has been reasonably reestablished, the patient may be weaned from the drugs that are administered or coadministered to ward off opportunistic infections. During the process of weaning from these drugs, and from HAART and the inventive therapeutic agents, for that matter, the patient should be closely monitored for signs of relapse. Such signs include increasing active HIV load, abnormal T cell counts, symptoms of opportunistic infections, etc. If signs of relapse are seen, then the patient should not be weaned from their medications for a further evaluation period. It may be necessary to make further adjustments to the patient's therapy, up to and including repeating practice of the present invention to eliminate residual reservoirs of HIV.

If the patient is successfully weaned from the last of the HAART, inventive therapeutics, and drugs to ward off opportunistic infections, and the patient's immune system is stable, then it may be possible for the patient to be in remission for long periods of time. Of course, during that time, the patient should be routinely monitored for reemergent signs of infection. If such signs reemerge, then the patient may require repeat treatments according to the invention.

In another embodiment, the invention may be practiced in an in vitro or ex vivo environment. All of the discussion above that is relevant to an in vitro or ex vivo environment applies to such embodiments. In particular, practice of an in vitro or ex vivo embodiment of the invention might be useful in the practice of immune system transplants, such as bone marrow transplants or peripheral stem cell procurement. In such procedures, the inventive therapeutic agents might be used, as generally described above, to purge the transplant material to reduce the risk of HIV infection due to HIV-infected memory T cells. In another embodiment, practice of the invention might be used to purge whole blood supplies to reduce the risk of HIV infection due to HIV-infected memory T cells. Other such in vitro or ex vivo applications will occur to one of skill in the art and are therefore contemplated as being within the scope of the invention.

It will be apparent to those skilled in the art that various modifications and variations can be made in the methods, kits and compositions of the present invention without departing from the spirit or scope of the invention. Thus, it is intended that the present invention cover the modifications and variations of this invention provided they come within the scope of the appended claims and their equivalents. Additionally, the following examples are appended for the purpose of illustrating the claimed invention, and should not be construed so as to limit the scope of the claimed invention.

EXAMPLES

Example 1

An individual with AIDS maintained on HAART therapy for a period of several months presents with low to non-detectable HIV viral loads (RNA PCR) in the plasma as measured by PCR techniques, and increased CD4+ counts. Next, CD4+RO+ cells are enriched by magnetic separation and FACS sorting, and assayed to determine infectivity with respect to naive and uninfected cell co-culture experiments. This analysis of CD4+RO+ memory cells shows the presence of infective HIV.

Pentostatin is therefore administered at a dose of 4 mg/m$^2$ by intravenous infusion once every two weeks for a period of 3 months until CD4+ cells, including memory cells, are at low levels. During administration of pentostatin and for a period of approximately 1–2 months thereafter, or until CD4+ cells recover, the patient is maintained on a maintenance dose of HAART, along with antibiotics and antifungal therapy. Stem cell or precursor cell replacement is provided through a bone marrow transplant and cytokine therapy, both of which are performed according to conventional techniques.

During and following therapy, the patient is followed at frequent intervals and monitored for CD34 cell level, reestablishment of CD4+ cells and quantitation of CD4+RO+ cells. Additionally, the patient's plasma is assayed for viral load by cell co-culture experiments. On reducing virus load in active and memory CD4+ T cells to low or non-detectable concentrations, the patient is weaned from pentostatin and HAART. After 3 months, the patient is weaned from antibiotic and antifungal therapy. Following this, the patient is followed at 6 month intervals and assayed for viral content.

Example 2

An individual with AIDS maintained on HAART therapy for a period of several months presents with low to non-detectable HIV viral loads (RNA PCR) in the plasma as measured by PCR techniques, and increased CD4+ counts. Next, CD4+RO+ cells are enriched by magnetic separation and FACS sorting, and assayed to determine infectivity with respect to naive and uninfected cell co-culture experiments. This analysis of CD4+RO+ memory cells shows the presence of infective HIV.

Fludarabine is injected intravenously at a dose of 10 mg/m$^2$ for a period of 5 days every 28 days to the patient until CD4+ cells, including memory cells, are at low levels. During administration of fludarabine, and for a period of approximately 1–2 months thereafter, or until CD4+ cells recover, the patient is maintained on a maintenance dose of HAART, along with antibiotics and antifungal therapy. Stem cell or precursor cell replacement is provided through a bone marrow transplant and cytokine therapy, both of which are performed according to conventional techniques.

During and following therapy, the patient is followed at frequent intervals and monitored for CD34 cell level, reestablishment of CD4+ cells and quantitation of CD4+RO+ cells. Additionally, the patient's plasma is assayed for viral load by cell co-culture experiments. On reducing virus load in active and memory CD4+ T cells to low or non-detectable concentrations, the patient is weaned from fludarabine and HAART. After 3 months, the patient is weaned from antibiotic and antifungal therapy. Following this, the patient is followed at 6 month intervals and assayed for viral content.

Example 3

An individual with AIDS maintained on HAART therapy for a period of several months presents with low to non-detectable HIV viral loads (RNA PCR) in the plasma as measured by PCR techniques, and increased CD4+ counts. Next, CD4+RO+ cells are enriched by magnetic separation and FACS sorting, and assayed to determine infectivity with respect to naive and uninfected cell co-culture experiments. This analysis of CD4+RO+ memory cells shows the presence of infective HIV.

Therapy is initiated in the patient utilizing a monoclonal antibody specific for CD4+ memory cells (RO+/HLA DR-) by intravenous route at 5 mg/kg doses once per day for 3–5 administrations, until CD4+ memory cells are significantly reduced by endogenous complement lysis or cell mediated clearance mechanisms. The antibody is obtained using similar techniques to those set forth in the discussion of the CD4+ specific antibody cM-T412 in N. Llewellyn-Smith, et al., "Effects of anti-CD4 antibody treatment on lymphocyte subsets and stimulated tumor necrosis factor alpha production: a study of 29 multiple sclerosis patients entered into a clinical trial of Cm-T412", *Neurology*, 48:810–816 (1997).

Therapy continues for a period of 3 months until CD4+ cells, including memory cells, are at low levels. During administration of the antibody, and for a period of approximately 1–2 months thereafter, or until CD4+ cells recover, the patient is maintained on a maintenance dose of HAART, along with antibiotics and antifungal therapy. Stem cell or precursor cell replacement is provided through a bone marrow transplant and cytokine therapy, both of which are performed according to conventional techniques.

During and following therapy, the patient is followed at frequent intervals and monitored for CD34 cell level, reestablishment of CD4+ cells and quantitation of CD4+RO+ cells. Additionally, the patient's plasma is assayed for viral load by cell co-culture experiments. On reducing virus load in active and memory CD4+ T cells to low or nondetectable concentrations, the patient is weaned from antibody therapy and HAART. After 3 months, the patient is weaned from antibiotic and antifungal therapy. Following this, the patient is followed at 6 month intervals and assayed for viral content.

Example 4

An individual with AIDS maintained on HAART therapy for a period of several months presents with low to non-detectable HIV viral loads (RNA PCR) in the plasma as measured by PCR techniques, and increased CD4+ counts. Next, CD4+RO+ cells are enriched by magnetic separation and FACS sorting, and assayed to determine infectivity with respect to naive and uninfected cell co-culture experiments. This analysis of CD4+RO+ memory cells shows the presence of infective HIV.

Therapy is initiated in the patient utilizing a monoclonal antibody conjugate specific for CD4+ memory cells (RO+/HLA DR-) by intravenous route at 5 mg/kg doses once per day for 3–5 administrations, until CD4+ memory cells are significantly reduced by endogenous complement lysis or cell mediated clearance mechanisms.

The monoclonal antibody conjugate is a conjugate of an antibody specific for CD4+-memory cell antigens together with ricin. The antibody is obtained using similar techniques to those set forth in the discussion of the CD4+ specific antibody cM-T412 in N. Llewellyn-Smith, et al., "Effects of anti-CD4 antibody treatment on lymphocyte subsets and stimulated tumor necrosis factor alpha production: a study of 29 multiple sclerosis patients entered into a clinical trial of Cm-T412", *Neurology*, 48:810–816 (1997). The ricin Mab conjugate is constructed using conventional techniques.

Therapy continues for a period of 3 months until CD4+ cells, including memory cells, are at low levels. During administration of the antibody conjugate, and for a period of approximately 1–2 months thereafter, or until CD4+ cells recover, the patient is maintained on a maintenance dose of HAART, along with antibiotics and antifungal therapy. Stem cell or precursor cell replacement is provided through a bone marrow transplant and cytokine therapy, both of which are performed according to conventional techniques.

During and following therapy, the patient is followed at frequent intervals and monitored for CD34 cell level, reestablishment of CD4+ cells and quantitation of CD4+RO+ cells. Additionally, the patient's plasma is assayed for viral load by cell co-culture experiments. On reducing virus load in active and memory CD4+ T cells to low or nondetectable concentrations, the patient is weaned from antibody conjugate therapy and HAART. After 3 months, the patient is weaned from antibiotic and antifungal therapy. Following this, the patient is followed at 6 month intervals and assayed for viral content.

Example 5

An individual with AIDS maintained on HAART therapy for a period of several months presents with low to nondetectable HIV viral loads (RNA PCR) in the plasma as measured by PCR techniques, and increased CD4+ counts. Next, CD4+RO+ cells are enriched by magnetic separation and FACS sorting, and assayed to determine infectivity with respect to naive and uninfected cell co-culture experiments. This analysis of CD4+RO+ memory cells shows the presence of infective HIV.

Cyclosporine is administered orally at a dose of 12 mg/kg/day and continued at this dose level on a daily basis for 2 weeks. This dose is tapered by 5% per week to a maintenance dose of 8 mg/kg/day. for a period of 3 months until CD4+ cells, including memory cells, are at low levels. During administration of cyclosporine and for a period of approximately 1–2 months thereafter, or until CD4+ cells recover, the patient is maintained on a maintenance dose of HAART, along with antibiotics and antifungal therapy. Stem cell or precursor cell replacement is provided through a bone marrow transplant and cytokine therapy, both of which are performed according to conventional techniques.

During and following therapy, the patient is followed at frequent intervals and monitored for CD34 cell level, reestablishment of CD4+ cells and quantitation of CD4+RO+ cells. Additionally, the patient's plasma is assayed for viral load by cell co-culture experiments. On reducing virus load in active and memory CD4+ T cells to low or non-detectable concentrations, the patient is weaned from cyclosporine and HAART. After 3 months, the patient is weaned from antibiotic and antifungal therapy. Following this, the patient is followed at 6 month intervals and assayed for viral content.

Example 6

An individual with AIDS maintained on HAART therapy for a period of several months presents with low to nondetectable HIV viral loads (RNA PCR) in the plasma as measured by PCR techniques, and increased CD4+ counts. Next, CD4+RO+ cells are enriched by magnetic separation and FACS sorting, and assayed to determine infectivity with respect to naive and uninfected cell co-culture experiments. This analysis of CD4+RO+ memory cells shows the presence of infective HIV.

Pentostatin is therefore coadministered in combination with 2', 3'-dideoxyadenosine (ddAdo). Pentostatin is administered intravenously at 4–5 mg/m² and ddAdo is administered intravenously at 5–7 mg/m² every two weeks for a period of 3 months until CD4+ cells, including memory cells, are at low levels.

During administration of pentostatin and ddAdo and for a period of approximately 1–2 months thereafter, or until CD4+ cells recover, the patient is maintained on a maintenance dose of HAART, along with antibiotics and antifungal therapy. Stem cell or precursor cell replacement is provided through a bone marrow transplant and cytokine therapy, both of which are performed according to conventional techniques.

During and following therapy, the patient is followed at frequent intervals and monitored for CD34 cell level, reestablishment of CD4+ cells and quantitation of CD4+RO+ cells. Additionally, the patient's plasma is assayed for viral load by cell co-culture experiments. On reducing virus load in active and memory CD4+ T cells to low or nondetectable concentrations, the patient is weaned from pentostatin, ddAdo and HAART. After 3 months, the patient is weaned from antibiotic and antifungal therapy. Following this, the patient is followed at 6 month intervals and assayed for viral content.

What is claimed is:

1. A method of treating an HIV-infected patient comprising:

treating the HIV-infected patient with HAART until the patient's viral load of active HIV in the plasma is at a low or undetectable level which is below 200 copies of HIV RNA per ml of plasma as determined by using PCR techniques; and then administering to the patient a therapeutic agent that is cytotoxic or cytostatic with respect to CD4+ T cells, but has reduced cytotoxic or cytostatic activity with respect to T lymphocyte stem cells, in a CD4+ T cell cytotoxic or cytostatic effective amount, wherein the therapeutic agent is selected from the group consisting of pentostatin, fludarabine and cladribine.

2. The method of claim 1 where the CD4+ T cell comprises a memory cell.

3. The method of claim 1, where the CD4+ T cells comprise both HIV-infected and non-HIV-infected CD4+ T cells.

4. The method of claim 1, wherein the therapeutic agent is administered or coadministered parenterally, intraperitoneally, intravenously, intraartierally, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

5. The method of claim 1, wherein the therapeutic agent is administered or coadministered singly or as a combination with another therapeutic agent.

6. The method of claim 5, wherein the combination comprises a deoxyadenosine and pentostatin.

7. The method of claim 6, wherein the combination comprises 2', 3'-dideoxyadenosine and pentostatin.

8. The method of claim 1, wherein the therapeutic agent is pentostatin, and the pentostatin is administered or coadministered intravenously in doses of about four to ten mg/sq m once per day for about three consecutive days once per month, about four to five mg/sq m/day weekly for about four weeks and about fortnightly thereafter, to the generally frequented dose of about four mg/sq m about every two weeks for a maximum dosage period of about one year.

9. The method of claim 1, wherein the reduced plasma HIV-1 viral load is undetectable by using PCR techniques.

10. The method of claim 1, further comprising monitoring viral load of active HIV in the plasma of the patient.

11. The method of claim 10, wherein monitoring viral load of active HIV includes monitoring the plasma viral load by using PCR techniques.

* * * * *